US008791089B2

(12) United States Patent
Groenendijk et al.

(10) Patent No.: US 8,791,089 B2
(45) Date of Patent: *Jul. 29, 2014

(54) SUPPORTING ACTIVITIES OF DAILY LIVING

(71) Applicant: N.V. Nutricia, Zoetermeer (NL)

(72) Inventors: Martine Groenendijk, Barendrecht (NL); Mattheus Cornelis de Wilde, Elst (NL); Robert Johan Joseph Hageman, Wageningen (NL); Patrick Joseph Gerardus Hendrikus Kamphuis, Utrecht (NL)

(73) Assignee: N.V. Nutricia, Zoetermeer (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/745,501

(22) Filed: Jan. 18, 2013

(65) Prior Publication Data

US 2013/0203646 A1  Aug. 8, 2013

Related U.S. Application Data

(63) Continuation of application No. 12/666,621, filed as application No. PCT/NL2008/050406 on Jun. 20, 2008, now Pat. No. 8,361,989.

(30) Foreign Application Priority Data

Jun. 26, 2007  (WO) ................ PCT/NL2007/050307

(51) Int. Cl.
*A01N 43/04* (2006.01)
*A61K 31/70* (2006.01)

(52) U.S. Cl.
USPC ................................. 514/50; 514/43; 514/49

(58) Field of Classification Search
None
See application file for complete search history.

(56) References Cited

U.S. PATENT DOCUMENTS

| 3,600,197 | A | 8/1971 | Spangler et al. |
|---|---|---|---|
| 5,378,488 | A | 1/1995 | Dimler et al. |
| 5,886,037 | A | 3/1999 | Klor et al. |
| 6,689,467 | B1 | 2/2004 | Joubert et al. |
| 6,835,750 | B1 | 12/2004 | Henderson |
| 7,090,879 | B2 | 8/2006 | Albrecht et al. |
| 8,282,965 | B2 | 10/2012 | De Kort et al. |
| 8,283,335 | B2 | 10/2012 | Hageman et al. |
| 8,361,989 | B2 | 1/2013 | Groenendijk et al. |
| 2003/0114415 | A1 | 6/2003 | Wurtman et al. |
| 2004/0001817 | A1 | 1/2004 | Giampapa |
| 2005/0208179 | A1 | 9/2005 | Albrecht et al. |
| 2006/0025376 | A1 | 2/2006 | Wurtman |
| 2006/0241077 | A1 | 10/2006 | Wurtman et al. |
| 2007/0004670 | A1 | 1/2007 | Wurtman et al. |
| 2007/0140992 | A1 | 6/2007 | Schick et al. |
| 2010/0323982 | A1 | 12/2010 | Hageman et al. |
| 2010/0331258 | A1 | 12/2010 | Kamphuis et al. |
| 2011/0006917 | A1 | 1/2011 | Taniguchi et al. |
| 2011/0105594 | A1 | 5/2011 | De Kort et al. |
| 2013/0012469 | A1 | 1/2013 | De Kort et al. |
| 2013/0018012 | A1 | 1/2013 | Hageman et al. |

FOREIGN PATENT DOCUMENTS

| EP | 0 175 468 A2 | 3/1986 |
|---|---|---|
| EP | 0 891 719 A1 | 1/1999 |
| EP | 1 216 041 B1 | 2/2004 |
| EP | 1 656 839 A1 | 5/2006 |
| EP | 1 666 092 A2 | 6/2006 |
| EP | 1 800 675 A1 | 6/2007 |
| EP | 1 282 365 B1 | 12/2007 |
| JP | 64-080250 A | 3/1989 |
| JP | 06-237734 A | 8/1994 |
| JP | 10-004918 A | 1/1998 |
| JP | 10-136937 A | 5/1998 |
| JP | 11-071274 A | 3/1999 |
| JP | 3-576318 B2 | 10/2004 |
| WO | WO-00/38829 A1 | 7/2000 |
| WO | WO-01/32034 A1 | 5/2001 |
| WO | WO-01/82928 | 11/2001 |
| WO | WO-02/088159 A1 | 11/2002 |
| WO | WO-02/096464 A1 | 12/2002 |
| WO | WO-03/013276 A1 | 2/2003 |
| WO | WO-03/041701 A2 | 5/2003 |
| WO | WO-2005/039597 A2 | 5/2005 |
| WO | WO-2006/031683 A2 | 3/2006 |
| WO | WO-2006/118665 A2 | 11/2006 |
| WO | WO-2006/127620 A1 | 11/2006 |
| WO | WO-2006/127620 A2 | 11/2006 |
| WO | WO-2007/001883 A2 | 1/2007 |
| WO | WO-2007/004685 A2 | 1/2007 |
| WO | WO-2007/004689 A1 | 1/2007 |
| WO | WO-2007/008586 A2 | 1/2007 |

(Continued)

OTHER PUBLICATIONS

"Derivative—Definition and More from the Free Merriam-Webster Dictionary" Retrieved Oct. 22, 2012 from http/www.merriam-webster.com/dictionary/derivative.
Albert, M. et al. "Preclinical prediction of AD using neuropsychological tests", Journal of the International Neuropsychological Society, 2001, vol. 7, pp. 631-639.
Bird, T.D., Genetic aspects of Alzheimer disease, Genetics in Medicine, Apr. 2008, vol. 10, No. 4, p. 231-237.

(Continued)

*Primary Examiner* — Patrick Lewis
(74) *Attorney, Agent, or Firm* — Gilberto M. Villacorta; Sunit Talapatra; Foley & Lardner LLP

(57) ABSTRACT

The invention provides a method for supporting operational activities in daily living by providing a combination of (a) long-chain polyunsaturated fatty acids, particularly DHA and/or EPA, and (b) nucleosides or nucleotides, particularly uridine or its equivalent. The operational activities comprise eating; walking; toileting; bathing; grooming; dressing; use of communication equipment; making conversations; keeping appointments; use of household appliances; cleaning dishes; preparation of meal or drink; writing; reading; independent housekeeping; transportation and shopping.

13 Claims, 2 Drawing Sheets

(56) References Cited

FOREIGN PATENT DOCUMENTS

| WO | WO-2007/058538 A2 | 5/2007 |
| --- | --- | --- |
| WO | WO-2007/073178 A2 | 6/2007 |
| WO | WO-2009/002145 A1 | 12/2008 |
| WO | WO-2009/002148 A1 | 12/2008 |
| WO | WO-2009/002163 A1 | 12/2008 |
| WO | WO-2009/002164 A1 | 12/2008 |
| WO | WO-2009/002165 A1 | 12/2008 |
| WO | WO-2009/002166 A1 | 12/2008 |
| WO | WO-2009/082203 A1 | 7/2009 |
| WO | WO-2009/082227 A1 | 7/2009 |

OTHER PUBLICATIONS

Cansev, M. et al. "Chronic Administration of Docosahexaenoic Acid or Eicosapentaenoic Acid, But Not Arachidonic Acid, Alone or in Combination with Uridine, Increases Brain Phosphatide and Synaptic Protein Levels in Gerbils", Neuroscience, 2007, vol. 148, pp. 421-431.
Cansev, M. et al. "Oral administration of circulating precursors for membrane phosphatides can promote the synthesis of new brain synapses", Alzheimer's & Dementia, 2008, vol. 4, pp. S153-S168.
Cole, G. et al. "Docosahexaenoic Acid Protects From Amyloid and Dendritic Pathology in an Alzheimer's Disease Mouse Model", Nutrition and Health, 2006, vol. 18, pp. 249-259.
Database WPI Week 198918, Derwent Publications Ltd., London, GB, AN 1989-134762, JP 01 080250, Mar. 27, 1989 [XP002449815].
Database WPI Week 199182, Derwent Publications Ltd., London, GB, AN 1998-123754, JP 10 004918, Jan. 13, 1998 [XP002470089], 1 page.
Database WPI Week 199439, Thomson Scientific, London, GB, AN 1994-312783, JP 06 237734, Aug. 30, 1994 [XP002494932], 2 pages.
Database WPI Week 199831, Derwent Publications Ltd., London, GB, AN 1998-355002, JP 10 136937, May 26, 1998 [XP002449814].
Database WPI Week 199921, Thomson Scientific, London, GB, AN 1999-248435, JP 11 071274, Mar. 16, 1999 [XP002495741].
Diagnostic and Statistical Manual of Mental Disorders (fourth Edition, 2000) 013 DSM-IV-TR; American Psychiatric Association. (table of contents only).
Folstein et al., "'Mini-Mental State' A Practical Method for Grading the Cognitive State of Patients for the Clinician," J Psychiat Res, 1975, 12(3), pp. 189-198.
Freund-Levi, Y. et al. "w-3 Fatty Acid Treatment in 174 Patients With Mild to Moderate Alzheimer Disease: OmegAD Study", Arch Neurol, Oct. 2006, vol. 63, pp. 1402-1408.
Galasko et al., "An Inventory to Assess Activities of Daily Living for Clinical Trials in Alzheimer's Disease," Alz Dis Assoc Dis, 1997, 11(Sup 2), pp. 33-39.
Hansson et al., "Association Between CSF Biomarkers and Incipient Alzheimer's Disease in Patients with Mild Congnitive Impairment: A Follow-up Study," Lancet Neurol, vol. 5, No. 3, 2006, pp. 228-234.
Holguin, S. et al. "Chronic adminstration of DHA and UMP improves the impaired memory of environmentally impoverished rats", Behavioural Brain Research, 2008, vol. 191, pp. 11-16.
Katoku et al., "Nutrient Compositions Containing Nucleic Acid Related Compounds, used for Growth and Health Maintenance—Contain e.g. Docosahexaenoic Acid, Arachidonic Acid and Cholesterol" WPI/Thomson, Jan. 1, 1900 [XP002470089].
Korezyn, A. et al. "The prevention of the dementia epidemic", Journal of the Neurological Sciences, 2007, vol. 257, pp. 2-4.
Markesbery, W. et al. "Neuropathologic Substrate of Mild Cognitive Impairment", Arch Neurol, Jan. 2006, vol. 63, pp. 38-46.
McKahnn et al., "Clinical diagnosis of Alzheimer's disease: Report of the NINCDS-ADRDA Work Group," Neurology, 1984, 34, pp. 939-944.
Morris, J. "Mild Cognitive Impairment Is Early-Stage Alzheimer Disease", Arch Neurol., 2006, vol. 63, No. 1, 6 pgs.
Nitsch, R. et al. "Evidence for a membrane defect in Alzheimer disease brain", Proc. Natl. Acad. Sci., Mar. 1992, vol. 89, pp. 1671-1675.
Oksman, M. "Impact of different saturated fatty acid, polyunsaturated fatty acid and cholesterol containing diets on beta-amyloid accumulation in APP/PS1 transgenic mice", Neurobiology of Disease, 2006, vol. 23, pp. 563-572.
Pratico et al., "Increase of Brain Oxidative Stress in Mild Cognitive Impairment," Arch Neurol, vol. 59, 2002, pp. 972-976.
Quadri et al. "Homocysteine, folate, and vitamin B-12 in mild cognitive impairment, Alzheimer disease, and vascular dementia", Am. J. Clin. Nutr., 2004, vol. 80, pp. 114-122.
Reynolds, E. "Vitamin B12, folic acid, and the nervous system", Review, Nov. 2006, vol. 5, pp. 949-960.
Sakamoto, T. et al. "Oral supplementation with docosahexaenoic acid and uridine-5'-monophosphate increases dendritic spine density in adult gerbil hippocampus", Brain Research, 2007, vol. 1182, pp. 50-59.
Wood-Kaczmar et al. Understanding the molecular causes of Parkinson's disease, Trends in Molecular Medicine, vol. 12, No. 11 (2006), pp. 521-528.
Wurtman et al., "Synaptic Proteins and Phospholipids are Increased in Gerbil Brain by Administering Uridine Plus Docosahexaenoic Acid Orally," Brain Research, 2006, 1088(1), pp. 83-92.
Cormier, et al. "Diet and Child Behavior Prolems: Fact or Fiction?", Pediatric Nursing, Mar.-Apr. 2007, vol. 33, No. 2, pp. 138-143.
Freemantle, et al. "Omega-3 fatty acids, energy substrates, and brain function during aging", Prostaglandins Leukotrienes and Essential Fatty Acids, 2006, vol. 75, pp. 213-220.
Purina Garden Recipe, http://purinasmallanimals.com/SmallAnimals/Gerbil/PurinaGardenRecipeGerbiland . . . , retrieved Oct. 15, 2013, 4 pgs.
US Office Action Dtd Nov. 19, 2013.
US Office Action Dtd Oct. 24, 2013.

SUPPORTING ACTIVITIES OF DAILY LIVING

CROSS-REFERENCE TO RELATED PATENT APPLICATIONS

This application is a Continuation of U.S. application Ser. No. 12/666,621, filed May 11, 2010, now U.S. Pat. No. 8,361,989, which is the National Stage application of International Application No. PCT/NL2008/050406, filed Jun. 20, 2008, which claims the benefit and priority of International Application No. PCT/NL2007/050307, filed Jun. 26, 2007. The foregoing applications are incorporated by reference herein in their entirety.

FIELD OF THE INVENTION

The invention relates to preparations, which comprise long chain polyunsaturated fatty acids and/or nucleotides or their equivalents, and which support the activities of daily living.

BACKGROUND OF THE INVENTION

Neuropathies or neurological problems may find their cause in aging, in prevalent pathologies in the brain, like those associated with the formation of plaques or neurofibrillary tangles in the brain. In many occasions neuropathies or neurological problems lead to a loss of independency and a need to provide extra care or a need to move the person to a nursing home or the like, in order to ensure a sustainable life of these persons.

WO02/088159 describes the neuroprotective effect of a lipoic acid derivative of uridine. WO2006/031683 relates to methods of improving cognitive and neurological functions and increasing synthesis and release of neurotransmitters and membrane synthesis by neural cells and brain cells, comprising administering a composition comprising a uridine. WO2007/004685 describes a composition containing DHA and arachidonic acid that has an activity of ameliorating reduced higher brain functions resulting from organic brain lesions. WO2007/004689 discloses a composition having an activity of ameliorating the reduced amount of diurnal activity and/or depressive symptoms, comprising arachidonic acid and/or a compound having arachidonic acid as a constituent fatty acid. US2007/0004670 describes methods of improving memory, learning, cognition, synaptic transmission and synthesis and release of neurotransmitters and increasing brain phospholipid levels in a subject. WO2006/127620 discloses a composition comprising DHA and UMP for the treatment of a subject with a memory disorder, learning problems, or a neurological disorder, such as an Alzheimer patient.

Wurtman et al., Brain Research 2006, 1088(1), 83-92 disclose a combination of choline, UMP and DHA as being able to enhance the quantity of synaptic proteins and phospholipids in gerbil brains and being potentially useful in treating Alzheimer's disease. EP1 656 839 discloses a composition for feeding infants of a mother who suffered from metabolic disorders during pregnancy, comprising inter alia DHA, EPA, uridine and choline. WO2007/058538 discloses a composition for treating a number of diseases such as AIDS, diarrhoea, etc. wherein said composition comprises inter alia a) DHA and EPA, b) uridine and c) choline. EP1 666 092 discloses a combination of DHA and uridine for the treatment of Alzheimer, depression and/or diabetes. JP3-576318 B2 discloses a nutritional composition for favourable growth and maintenance of healthy conditions comprising DHA and UMP. WO03/041701 discloses a composition comprising DHA, EPA, choline, methionine, vitamin B6, folic acid, zinc, magnesium and UMP as alternative for nucleobases for the treatment of Parkinson's disease, epilepsy, schizophrenia, paranoia, depression, sleep disorders, psychoses, dementia, ADHA, impaired memory function, chronic fatigue syndrome and motor disorders.

None of the above documents discloses the improvement of activities of daily living, as defined in this invention. Moreover, it is imperative to understand that the invention is not concerned with the treatment of Alzheimer's disease or dementia itself, but with the treatment of persons suffering from Alzheimer's disease, dementia and/or elderly.

SUMMARY OF THE INVENTION

The present inventors found that the administration of the present composition improves activities wherein the (i) operational activities and the executive brain functions play an important role (i.e. the instrumental and/or basic activities of daily living). Such activities include many activities that take place throughout the day, particularly housekeeping, personal hygiene practices and meal preparation. This finding particularly enables persons that are suffering from difficulty in performing such activities (e.g. humans suffering from Alzheimer's disease, dementia and/or non-dementing or dementing elderly) to prolong an independent way of living. The improvement in ability to perform the instrumental and/or basic activities of daily living is often considered more important than improving memory and/or cognitive function.

This finding is particularly unexpected as the coordination of these complex activities of daily living is coordinated by different parts of the brain, i.e. the operational parts of the activities are (mainly) coordinated by the motor cortex, the executive (e.g. planning) parts of the activities of daily living are (mainly) coordinated by the prefrontal cortex, while memory functions are (mainly) coordinated by the hippocampus and temporal cortex. Experimental results showed that administration of the present composition to subjects suffering from impaired brain functions (particularly Alzheimer's disease) restored the activities, to near normal levels. Hence, the present inventors found that the present composition has an important stimulatory effect on the instrumental and/or basic activities of daily living, particularly in humans suffering from Alzheimer's disease. The present composition supports and enable those complex activities where initiation, planning and effective operation performance play a role.

In a further aspect, the present inventors found, in addition to the above, that the present composition for supporting the activities of daily living advantageously comprises folic acid, vitamin B12 and/or vitamin B6, preferably in relatively high dosages. It was found that these vitamins can be advantageously included in the present invention. The administration of the B vitamins was found to decrease locomotor activity during the resting period, hence ensuring a good rest during the night. Hence, the present composition, when including B-vitamins advantageously supports the present activities of daily living, while providing a good resting period.

The present finding enables a solution for an important problem for humans suffering from Alzheimer's, dementia and/or aging (i.e. the elderly). Many subjects fear the time that they become dependent on the help and support from others when desiring to perform activities of daily living. Hence, for these subjects it is particularly desirable to extend the period of independence. The present inventors solved this problem by providing a (nutritional) composition that is easy to ingest, and enables a prolonged capacity to perform the relatively complex activities of daily living.

In particular, the present invention relates to improvements in independent performance of activities wherein the operational aspect has a dominant role. The present invention particularly relates to improvements in independent performance of the following activities: coordination of movements, particularly when eating or drinking; grasping goods; putting objects on a desired location/position; making rapid movements; walking; maintaining balance in body position; doing the laundry; doing the dishes.

In a further aspect the present invention relates to improvements in independent performance of activities wherein the operational aspect has a main role, in addition to other higher brain functions. The present invention particularly relates to improvements in independent performance of the following activities: using communication equipment, especially telephone; using household appliances, especially television; personal hygiene practices, particularly cutting nails, doing hair properly or apply shaving practices; dressing, preparing a meal, shopping, travelling.

It was found that particularly the administration of a preparation that comprises DHA and uridine results in the desired improvements. It is considered particularly advantageous to co-administer with the DHA and/or uridine at least one of vitamin B6, vitamin B12 and/or folic acid. Inclusion of these vitamins improves the effects of the administration of DHA and/or nucleotide. Further improvements can be achieved by co-administration of phospholipids. Without wishing to be bound by theory, the present inventors believe that the phospholipids enable effective membrane function, further improving effectiveness of the present composition in it's support for daily living activities.

At the same time, the present product preferably is formulated so that it has a relatively low impact on appetite and consumption patterns of other food, and is easy to consume. It preferably does not comprise herb extracts, which may be varying in quality, and under normal circumstances are difficult to include in stable sterilized liquid products and may comprise components which have a badly defined biological action.

DETAILED DESCRIPTION OF PREFERRED EMBODIMENTS

Figure 1:
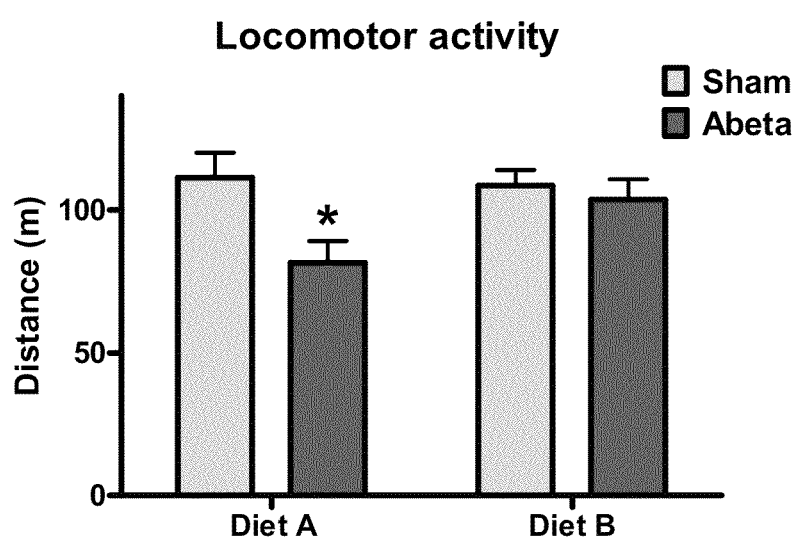
FIG. 1 shows relative locomotor activity in abeta-infused and "sham" rats on diet A (control) versus diet B (experiment).

The present invention provides the use of a composition comprising (a) DHA and/or EPA, and (b) uridine or its equivalent, in the manufacture of a composition for supporting activities in daily living. Alternatively the present invention provides a method for supporting activities in daily living, said method comprising administering to a patient (particularly a patient suffering from Alzheimer's disease) a composition comprising (a) DHA and/or EPA, and (b) uridine or its equivalent.

In a further aspect the present invention provides a liquid composition comprising per 100 ml, 0.2-2 gram uridine of an uridine equivalent; 0.5-5 g DHA; 0.5-10 g protein; 2-20 g carbohydrates; 0.5-15 microgram vitamin B12; 50-1000 microgram folic acid and 0.1-10 mg vitamin B6, wherein the composition has a viscosity of 1-40 mPas measured at a shear rate of 100 per sec at 20° C.; an osmolality of 300 to 800 mOsm/kg and a caloric density between 0.2 and 3 kcal/ml.

LC-PUFA

The present invention comprises the use of long chain polyunsaturated fatty acids (LCP), preferably at least one LCP selected from docosahexaenoic acid (22:6 ω-3; DHA), docosapentaenoic acid (22:5 ω-3; DPA) and eicosapentaenoic acid (20:5 ω-3; EPA). Preferably the present composition contains at least DHA, preferably DHA and EPA. More preferably the composition contains DHA and at least one precursor of DHA selected from EPA and DPA, more preferably the present composition comprises DHA, DPA and EPA. The inventors recognized that only part of the DHA incorporated in the brain is from orally ingested DHA. An important part of the DHA incorporated in the brain is derived from conversion of DPA to DHA in the brain. In a further aspect the present composition preferably contains a significant amount of EPA. EPA is converted to DPA (ω-3), increasing subsequent conversion of DPA (ω-3) to DHA in the brain. Hence, the present composition preferably also contains a significant amount of EPA, so to further stimulate in-vivo DHA formation.

The LCP is preferably provided as triglycerides, diglycerides, monoglycerides, free fatty acids or their salts or esters, phospholipids, lysophospholipids, glycerol ethers, lipoproteins, ceramides, glycolipids or combinations thereof. Preferably, the present composition comprises at least DHA in triglyceride form.

The present method preferably comprises the administration of 400-5000 mg (DHA+EPA) per day, more preferably 500-3000 mg per day. The proportion of (DHA+EPA) of the total fatty acids is preferably 5-50 wt. %, more preferably 10-45 wt. %, most preferably 15-40 wt. %. The present method preferably comprises the administration of DHA, preferably in an amount of 300-4000 mg per day, more preferably 500-2500 mg per day. The present method preferably comprises the administration of DHA, preferably a composition comprising 300-4000 mg DHA per 100 ml day, more preferably 500-2500 mg DHA per 100 ml. The present composition preferably comprises 1-40 wt. % DHA based on total fatty acids, preferably 3-36 wt. % DHA based on total fatty acids, more preferably 10-30 wt. % DHA based on total fatty acids. The present composition preferably comprises 0.5-20 wt. % EPA based on total fatty acids, preferably 2-10 wt. % EPA based on total fatty acids, more preferably 5-10 wt. % EPA based on total fatty acids. The ratio of the weights of DHA to the sum of EPA and DPA (ω-3) is preferably larger than 1.0, more preferably 1.2-10, most preferably 2-8. The above-mentioned ratios and amounts take into account and optimise several aspects, including taste (too high LCP levels reduce taste, resulting in a reduced compliance), balance between DHA and precursors thereof to ensure optimal effectiveness in relation to maximum dosage and possibility of product formulations such as liquid form, bar or capsule.

The present composition preferably contains a very low amount of arachidonic acid (AA; 20:4 ω-6). Arachidonic acid is believed to counteract the effects of the present composition. The subjects of the present method normally ingest sufficient (precursors of) AA, and an excess daily dosage may stimulate inflammatory responses, inhibiting activities of daily living. Preferably the weight ratio DHA/AA in the present composition is at least 5, preferably at least 10, more preferably at least 15, up to e.g. 60 or up to 30. The present method preferably comprises the administration of a composition comprising less than 5 wt. % arachidonic acid based on total fatty acids, more preferably below 2.5 wt. %, e.g. down to 0.5 wt. %. The ratio ω-6/ω-3 fatty acids (C 18 and higher)

in the present product is preferably below 0.5, more preferably below 0.2, e.g. down to 0.05 or to 0.1. The ratio ω-6/ω-3 fatty acids (C 20 and higher) in the present product is preferably below 0.3, more preferably below 0.15, e.g. down to 0.03 or to 0.06.

The present composition preferably contains at least one oil selected from fish oil, algal oil and eggs lipids. Preferably the present composition contains fish oil comprising DHA, EPA and preferably DPA.

Saturated and Monounsaturated Fatty Acids

The present composition preferably comprises saturated and/or mono-unsaturated fatty acids. The amount of saturated fatty acids is preferably 6-60 wt. % based on total fatty acids, preferably 12-40 wt. %, more preferably 20-40 wt. % based on total fatty acids. In particular the amount of C14:0 (myristic acid) +C16:0 (palmitic acid) is preferably 5-50 wt. %, preferably 8-36, more preferably 15-30 wt. % based on total fatty acids. The total amount of monounsaturated fatty acids, such as oleic acid and palmitoleic acid, is preferably between 5 and 40 wt. %, more preferably between 15 and 30 wt. %. Including of the saturated and/or monounsaturated fatty acids provides an energy source, improving the present activities of daily living.

Phospholipids

Preferably, the present composition preferably comprises phospholipids, preferably 0.1-50 wt. % phospholipids based on total weight of lipids, more preferably 0.5-20 wt. %, more preferably between 1 and 5 wt. % based on total weight of lipids. The total amount of lipids is preferably between 10 and 30 wt. % on dry matter, and/or between 2 and 6 g lipid per 100 ml for a liquid composition. Inclusion of phospholipids beneficially improves membrane function, thereby enabling an improved functioning of the different parts of the brain that play a (main) role in activities of daily living. Furthermore, the phospholipids improve stability of the present product.

Folic Acid, Vitamin B12 and/or Vitamin B6

The present composition preferably contain folic acid, vitamin B12 and/or vitamin B6, particularly in (relatively) high dosages. Inclusion of these vitamins advantageously provides the combination of support and enablement of activities of daily living, while providing a reduced locomotor activity during the resting period. Further advantage of co-administration of folic acid, vitamin B12 and/or vitamin B6 is that is relief's patients of deficiencies in these vitamins. Preferably the present composition comprises at least two selected from the group consisting of folic acid, vitamin B12 and/or vitamin B6. More preferably the present composition comprises folic acid, vitamin B12 and vitamin B6.

The present composition preferably comprises 50-1000 microgram folic acid per 100 g liquid product, more preferably 150-750 microgram folic acid per 100 g liquid product, more preferably 200-500 microgram folic acid per 100 g liquid product. The present method preferably comprises the administration 50-1000 microgram folic acid per day, more preferably 150-750 microgram folic acid per day, more preferably 200-500 microgram folic acid per day. The present composition preferably comprises 0.5-15 microgram vitamin B12 per 100 g liquid product, more preferably 1-10 microgram vitamin B12 per 100 g liquid product, more preferably 1.5-5 microgram vitamin B12 per 100 g liquid product. The present method preferably comprises the administration 0.5-15 microgram vitamin B12 per day, more preferably 1-10 microgram vitamin B12 per day, more preferably 1.5-5 microgram vitamin B12 per day. The present composition preferably comprises 0.1-10 mg vitamin B6 per 100 g liquid product, more preferably 0.4-5 mg vitamin B6 per 100 g liquid product, more preferably 0.6-5 mg vitamin B6 per 100 g liquid product. The present method preferably comprises the administration 0.1-10 microgram vitamin B6 per day, more preferably 0.5-5 mg vitamin B6 per day, more preferably 0.75-5 mg vitamin B6 per day.

Nucleotides

The present composition preferably comprises uridine and/or an equivalent thereof, preferably at least one uridine or an equivalent thereof selected from the group consisting of uridine (i.e. ribosyl uracil), deoxyuridine (deoxyribosyl uracil), uridine phosphates (UMP, dUMP, UDP, UTP), nucleobase uracil and acylated uridine derivatives. Preferably the present composition comprises one or more uridine phosphate selected from the group consisting of uridine monophosphate (UMP), uridine diphosphate (UDP and uridine triphosphate (UTP). Most preferably the present composition comprises UMP, as UMP is most efficiently being taken up by the body. Preferably at least 50 wt. % of the uridine in the present composition is provided by UMP, more preferably at least 75 wt. %, most preferably at least 95 wt. %. The present method preferably comprises the administration of uridine (the cumulative amount of uridine, deoxyuridine, uridine phosphates, nucleobase uracil and acylated uridine derivatives) in an amount of 0.08-3 g per day, preferably 0.1-2 g per day, more preferably 0.2-1 g per day.

Preferably the present composition comprises uridine phosphate, preferably uridine monophosphate (UMP). The UMP very efficiently taken up by the body. Hence, inclusion of UMP in the present product enables a high effectively at the lowest dosage and/or the administration of a low volume to the subject. Preferably the weight ratio of uridine to cytidine is larger that 1.0, more preferably 2.0, most preferably more than 5.0. The term uridine as used herein relates to uridine and/or equivalents thereof. The term cytidine as used herein relates to cytidine and/or equivalent thereof. Although cytidine is a precursor of uridine, which passes the blood brain barrier, it is more efficient and effective to include uridine in the present composition.

The present method preferably comprises the administration of uridine monophosphate (UMP) in an amount of 0.08-3 g per day, preferably 0.1-2 g per day, more preferably 0.2-1 g per day. The present method preferably comprises the administration of a composition comprising uridine in an amount of 0.08-3 g UMP per 100 ml liquid product, preferably 0.1-2 g UMP per 100 ml liquid product, more preferably 0.2-1 g per 100 ml liquid product. Preferably 1-37.5 mg UMP per kilogram body weight is administered per day. The required dosages of the equivalents on a weight base can be calculated from the dose for UMP by taking equimolar amounts using the molecular weight of the equivalent and of UMP, the latter being 324 Dalton. The amount of nucleotides or nucleosides and derivatives is preferably 3-115 μmol, preferably 5-35 μmol per kg body weight per day, or 0.25 to 9 mmol, preferably 0.3-6, most preferably 0.45-2.8 mmol per day.

Uridine derivatives like UDP, which is readily formed from dietetic UMP, appear to be important for transport of glycoproteins and glycolipids within the cell and availability thereof in the cytosol and plasma membrane.

In a further preferred embodiment the present composition preferably does not contain high amounts of other nucleotides. Hence, preferably the weight ratio adenosine/uridine in the present composition is below 0.1, more preferably below 0.01, most preferably 0. Preferably the weight ratio guanosine/uridine in the present composition is below 0.1, more preferably below 0.01, most preferably 0. Preferably the weight ratio inosine/uridine in the present composition is below 0.1, more preferably below 0.01, most preferably 0.

Combination of Uridine and LCP

It was found by the inventors that the nucleotide equivalents as defined, and in particular the uridine sources as defined are important to support and/or enhance the effect of the lipid fractions as defined above on activities of daily living. The present combination, particularly of (i) uridine and (ii) DHA and/or EPA is surprisingly effective. On a biochemical level this may be observed by an improvement of ceramide metabolism in membranes and in particular an increase in glycolipids at the expense of the presence of simple ceramides.

Methyl Donors

Preferably the present composition contains methyl donors. Methyl donors are those food grade compounds which are capable of providing a methyl, methylene or formyl group when administered to a human individual in vivo. The methyl donor included in the present composition is preferably selected from the group consisting of serine, methionine, choline, betaine, dimethylglycine and sarcosine and derivatives thereof. Preferably the present composition contains choline and/or phosphatidylcholine. The present method preferably comprises the administration of more than 50 mg choline per day, preferably 80-2000 mg choline per day, more preferably 120-1000 mg choline per day, most preferably 150-600 mg choline per day. The present composition preferably comprises 50 mg to 3 gram choline per 100 ml of the present liquid formula, preferably 200 mg-1000 mg choline/100 ml. The methyl donor (particularly choline) is an important precursor of the brain membrane and thereby enables a improved functioning of the brain area involved in supporting activities of daily living. In a particularly preferred embodiment the present composition comprises phospholipids and choline. It was found that the administration of phospholipids with choline results in maintenance of high choline level. As choline is an important precursor of muscle neurotransmitters, high choline levels (as a result of administration of phospholipids) support of daily living activities.

Minerals & Trace Elements

The present composition can be further improved by including one or more minerals. Preferably the present composition comprises at least one mineral selected from zinc, magnesium, copper, manganese and molybdenum. Preferably the present composition comprises manganese and molybdenum.

Manganese

Inclusion of manganese in a diet is important for improving membrane function of cells, in particular the membrane function of nerve cells. Especially those persons that are malnourished or have an inherited or metabolic disorder involving imparted metabolic capacity for producing sphingomyelin and/or related compounds like sulfatides and glycosylated ceramides, benefit from inclusion of the mineral fraction.

The amount of manganese administered per day is preferably more than 0.1 mg, more preferably 0.1-1 mg. Preferably the present method comprises the administration of a (liquid) composition comprising 0.05 to 2 mg manganese per 100 ml, preferably 0.1-1 mg manganese per 100 ml.

Molybdenum

Additional molybdenum is strongly preferred to allow proper functioning of the cofactors, which appears important for creating a proper composition of the membranes, e.g. their sulfatide content, and in particular ensures a proper functioning of nerve cells. Further, inclusion of a proper amount of molybdenum delays brain shrinkage in part of the elderly during aging. The present method preferably comprises the administration of a composition comprising 0.1-100 microgram molybdenum per 100 ml, preferably 1-50 µg molybdenum per 100 ml.

Zinc

It is also preferred to include additional zinc into the product which comprises the lipids or nucleotide fraction as described above, in order to stabilize proteins in the brain and prevent agglomeration thereof, which could impart daily life activities. The present method preferably comprises the administration of a composition comprising 0.05 mg-25 mg zinc per 100 ml, preferably 0.1-10 mg zinc per 100 ml.

Selenium

The present composition preferably contain selenium. The antioxidant activity of selenium advantageously prevents and/or inhibits damaged to the brain areas which enable activities of daily living. A low selenium levels increases the risk for hospitalisation, particularly in elderly and patients suffering from Alzheimer's disease. Preferably the present method provides the administration of a composition comprising 0.01 and 5 mg selenium per 100 ml liquid product, preferably 0.02 and 0.1 mg selenium per 100 ml liquid product. The amount of selenium administered per day is preferably more than 0.01 mg, more preferably 0.01-0.5 mg.

Product

The present composition is preferably a ready-to-use liquid, solid, or semi-liquid product. It can also be in a concentrated form suitable for dissolving or dilution or suitable for the purpose of fortifying a second product. The preparation can be a drink, an emulsion, a dispersion, a pill or capsule, a bar, a powder, granulated or not, a pudding, a sauce, a gel, an ice cream, a soup, a cookie, a lollipop, sweetie, or other form known in the art. The present composition is preferably enterally administered, more preferably orally. Most preferably the present composition is administered through a straw.

The subjects that can benefit from the method and composition of the invention (particularly patients suffering from Alzheimer's, dementia and/or elderly) often experience problems with eating. Their sensory capabilities and/or control of muscles has become imparted, as well as in some instances their ambition to apply proper eating habits. Swallowing and/or mastication are often problematic. The present invention therefore preferably has a low viscosity, preferably a viscosity between 1 and 2000 mPa·s measured at a shear rate of 100 $\sec^{-1}$ at 20° C. More preferably, the present composition is preferably provided in the form of a drink capable of being ingested through a straw which makes the product even easier to ingest and improves compliance. In a preferred embodiment the present composition has a viscosity of 1-80 mPas at a shear rate of 100 per sec at 20° C., more preferably of 1-40 mPas at a shear rate of 100 per sec at 20° C. To be optimally accepted by the patient, the present composition preferably has an osmolality of 300 to 800 mOsm/kg.

Additionally many of the subjects (e.g. suffering from Alzheimer's, dementia and/or elderly) experience a general loss in appetite and/or become malnourished. Hence it is advantageous to include within the present composition other nutrients. However, the energy density of the product is preferably not so high that it interferes with normal eating habits. When in liquid form, the present product preferably contains between 0.2 and 3 kcal/ml, more preferably between 0.5 and 2, between 0.7 and 1.5 kcal/mL Advantageously the present composition contains digestible carbohydrates. The digestible carbohydrates positively influence the operational skills of the subject, and have an advantageous effect over and above the effects for the present composition containing LCP and/or uridine. The present composition preferably contains between 1 and 50 gram digestible carbohydrates per 100 ml of a liquid product, more preferably between 5 and 30 grams per 100 ml, more preferably 10-30 grams carbohydrates/100 ml. The total amount of digestible carbohydrates is preferably between 25 and 80 wt. % on dry matter, preferably 40-80 wt. % based on dry matter.

The product is mainly administered to frail elderly, wherein muscle strength is preferably improved. The present composition preferably contains protein to improve muscle strength. The improved muscle strength provides an important stimulus for support of activities of daily living, and advantageously contributes to the present method. The present composition preferably contains 0.5-15 gram protein per 100 ml of the liquid product, preferably 1-10 grams per 100 ml of the liquid product, more preferably 1-5 grams per 100 ml of the liquid product. Preferably the present composition contains at least 80 wt. % milk derived protein (e.g. whey and/or casein) based on total protein.

The present method preferably comprises the administration of a composition of 50 to 250 ml, preferably 75 to 150 ml.

Subjects

The present composition is preferably administered to a human, more preferably to (i) an elderly human (dementing or non-dementing) and/or a human suffering from Alzheimer's disease, (senile) dementia, Parkinson's Disease, Multiple Sclerosis, aphasia, apraxia, ataxia, dystonia or dyskinesia. In this respect, it is submitted that in the context of this application, an elderly person is a person of the age of 50 or more, in particular of the age of 55 or more, more in particular of the age of 60 or more, more in particular of the age of 65 or more. This rather broad definition takes into account the fact that the average age varies between different populations, on different continents, etc. Most developed world countries have accepted the chronological age of 65 years as a definition of "elderly" or older person (associated with the age at which one may begin to receive pension benefits), but like many westernized concepts, this does not adapt well to e.g. the situation in Africa. At the moment, there is no United Nations (UN) standard numerical criterion, but the UN agreed cut-off is 60+ years to refer to the older population in Western world. The more traditional African definitions of an elder or "elderly" person correlate with the chronological ages of 50 to 65 years, depending on the setting, the region and the country.

The present method is particularly suitable for patients suffering from Alzheimer's disease and/or MCI. Preferably, the present composition is administered to a subject suffering from Alzheimer's, more preferably a subject suffering from early or mild Alzheimer's, preferably to a subject suffering from Alzheimer's disease, wherein said subject with a mini mental state examination (MMSE) score of 16 to 27, preferably 20 to 26. It was found that in this subgroup of Alzheimer patients the present composition was particularly effective. This patient group is often on the edge of loosing independence on the activities of daily living. Hence, restoring and improving the present skills of this group of patients have a particularly high benefit. The present method is also suitable for dementing and non-dementing elderly, in particular non-dementing elderly, for the same reasons as given above.

Uses

The present method particularly aims to (i) support and/or enhance the activities of daily living and/or prolonged independent living.

The term "activities of daily living" as used in the present invention relates to instrumental and/or basic activities of daily living. In particular the present invention provides a method for supporting and/or enhancing the instrumental and/or basic activities of daily living. Preferably at least one of the following instrumental activities of daily living is supported and/or enhanced: performing light and/or heavy housework, preparing meals and/or drinks, shopping for groceries, using household appliances (particularly the telephone) and taking medication. Preferably at least one of the following basic activities of daily living is supported or enhanced: personal hygiene activities (particularly washing and/or bathing), dressing, walking and/or using the toilet.

"Prolonging independent living" as used in the present invention can be easily determined by tests which determine the effect of a therapy on the time before the patient is moving to an institution. The present invention also relates to a method for increasing the time to nursing home admission, comprising administering the present composition. A further benefit of the present invention is a reduced caregiver burden.

In one aspect the present invention provides for a method (or use) of the present composition for improving the ability to/for: (i) eating, walking, toileting, bathing, grooming and/or dressing; and/or (ii) use of communication equipment (particularly telephone), making conversations, keeping appointments, use of household appliances (particularly television), cleaning dishes, preparation of meal or drink, writing, reading, independent housekeeping, transportation and/or shopping. Typically, the method of the invention aims at supporting or improving the capability of performing practical operations which more rely on motor capacities than on cognitive capacities. The method of the invention thus serves at improving quality of life.

The activities of daily living also include the power or capability to make rapid or secure movements, or to walk safely or without feelings of fear of falling on the ground or to maintain equilibrium of the body under those conditions that for young healthy persons give no problem. The support of these activities in persons in need of such support result in a maintenance, a restoration or a decrease in the decline of the capabilities to go out walking safely, to go shopping, walk timely to the bathroom or climb the stairs.

Other activities of daily living include sensory-motor skills, whose adequate presence becomes evident in the capability to coordinate movements of muscles or limbs, in particular during eating or drinking, while wanting to grasp goods, or while aiming to put things on an exact location or in a particular position. Support of these activities in persons in need of such support, is meant to be the maintenance, restoration or a decrease in the rate of decline of the capabilities to prepare or consume a meal, a drink.

The activities of daily life also include the capability to feel, notify, touch or clean all areas of the body. Support of these activities in persons in need of such support is meant to be a restoration, maintenance or decrease of the decline of feeling or full sensation of all parts of the body, of cleaning practices and of the application of hygienic practices of the person's own body and the person's environment.

Such support of the activities as occur in normal daily life, to a level which keeps the persons in a state of independency and/or self maintenance in the society, can be achieved by administration of an effective amount of the present composition.

The improvement of the activities of daily living can be measured. Activities of daily living can be measured using a number of tests, among which the Alzheimer's Disease Cooperative Study Activities of Daily Living Inventory (ADCS-ADL). This is a caregiver rated questionnaire of 23 items, with possible scores over a range of 0-78, where 78 implies full functioning with no impairment (see: Galasko, D; Bennett, D.; Sano, M.; Ernesto, C.; Thomas, R.; Grundman, M.; Ferris, S.; and the ADCS. An Inventory to Assess Activities of Daily Living for Clinical Trials in Alzheimer's Disease. Alzheimer's Disease and Associated Disorders, 1997. Volume 11(2): S33-S39). The questions relative in particular to eating (1); walking (2); toileting (3); bathing (4); grooming (5); selecting clothes and dressing (6); making telephone calls (7); watching television (8); making conversation (9); clearing dishes from a table (10); finding personal belongings (11); getting or preparing a beverage (12); preparing a meal or snack (13); disposing of garbage or litter (14); travelling (15); shopping (16); keeping appointments or meetings (17); being alone (18); talking about current events (19); reading (20); writing (21); pastime, hobby or game (22), and using household appliances (23). This test was used in the clinical test of Example 5.

In one embodiment the present invention provides the present composition together with instructions for (preferably oral) administration of the composition and indication that said product can be used for one or more of (i) supporting the activities of daily living and/or prolong independent living; or (ii) stimulating eating, walking, toileting, bathing, grooming and/or dressing; or (iii) stimulating use of communication equipment (particularly telephone), making conversations, keeping appointments, use of household appliances (particularly television), cleaning dishes, preparation of meal or drink, writing, reading, independent housekeeping, transportation and/or shopping In a further embodiment present invention provides the present composition together with instructions for (preferably oral) administration of the composition and indication that administration of the present composition provides the health benefit as described in a published scientific paper, said scientific paper describing a positive outcome for one or more of (i) supporting the activities of daily living and/or prolong independent living; or (ii) stimulating eating, walking, toileting, bathing, grooming and/or dressing; or (iii) stimulating use of communication equipment (particularly telephone), making conversations, keeping appointments, use of household appliances (particularly television), cleaning dishes, preparation of meal or drink, writing, reading, independent housekeeping, transportation and/or shopping

EXAMPLES

Example 1

In-vivo Study

Rats can be modelled for the capacity to deal with difficulties in instrumental and/or basic activities of daily living by infusing the rats with beta-amyloid, a protein causing toxicity in the brain leading to neuropathies, into the lateral ventricle of the brain. Rats infused this way show impairment in spontaneous activity in a new environment, which is an important part of activities of daily living, and indicative for the instrumental and/or basic activities of daily living in humans, particularly humans suffering from Alzheimer's disease. The infused rats do not explore the new environment as extensively as control rats do, which is reflected in reduced exploration time and a decrease in walking distance. This study uses a dietary composition (diet B) to overcome the difficulties in daily life activities.

Experimental Design

Four groups of rats received either an infusion into the lateral ventricle with beta-amyloid (Abeta) or a saline solution (Sham). Five weeks prior to the infusions the rats were fed one of two diets, A or B. The four groups are summarized in table 1. Table 2 lists the dietary composition of the two diets. Diet A serves as a control diet. Diet B is enriched in e.g. DHA, uridine and choline. The rats are placed in a new environment (circular arena, 120 cm in diameter) for 15 minutes and their walking pattern is analysed.

TABLE 1

Groups of rats differing in infusion solutions and diet.

| Group | Infusion | Diet |
|---|---|---|
| 1 | Sham | A |
| 2 | Abeta | A |
| 3 | Sham | B |
| 4 | Abeta | B |

TABLE 2

Composition of the diets.

| | | Diet A | Diet B |
|---|---|---|---|
| | | g/100 g fat | g/100 g fat |
| Fatty Acids | LA | 31.1 | 30.0 |
| | ALA | 1.3 | 2.9 |
| | EPA | — | — |
| | DHA | — | 3.3 |
| | total ω-6 | 31.1 | 30.4 |
| | total ω-3 | 1.3 | 13.0 |
| | ω-6/ω-3 | 23.5 | 2.3 |
| | | mg/100 g food | mg/100 g food |
| Phospho-lipids | Soya Lecithin | — | 500 |
| | of which PC | — | 130 |
| | of which PS | — | 20 |
| | | g/100 g food | g/100 g food |
| | Choline | — | 0.95 |
| | UMP | — | 1.55 |
| | | mg/100 g food | mg/100 g food |
| Vitamins | A | 400 | 400 |
| | D3 | 100 | 100 |
| | E | 3 | 253 |
| | K3 | 0.005 | 0.005 |
| | B1 | 0.4 | 0.4 |
| | B2 | 0.3 | 0.3 |
| | B6 | 0.6 | 4.725 |
| | B12 | 0.005 | 0.00575 |
| | Vitamin C | 0 | 200 |
| | Niacin | 2 | 2 |
| | Pantothenic acid | 0.8 | 0.8 |
| | Choline | 86.8 | 86.8 |
| | Folic acid | 0.1 | 1.35 |
| | Biotin | 0.2 | 0.2 |
| Minerals | Iron | 3.5 | 3.5 |
| | Copper | 0.4 | 0.4 |
| | Zinc | 1.2 | 1.2 |
| | Manganese | 5 | 5 |
| | Iodide | 0.015 | 0.015 |
| | Selenium | 0.009 | 0.159 |
| | Cobalt | 0 | 0 |
| | Chromium | 0.029 | 0.029 |
| | Nickel | 0.007 | 0.007 |
| | Fluorine | 0.09 | 0.09 |
| | Tin | 0.1 | 0.1 |
| | Vanadium | 0.009 | 0.009 |

Results

On the control diet (A) rats infused with abeta show decreased walking distance in the new environment. When fed the experimental diet (B) to abeta infused rats restored exploration of the new environment to levels of control rats (Sham operated rats, no abeta infusion). FIG. 1 shows that Abeta infused rats displayed ~25% reduced locomotor activity in the Open Field on diet A diet, but not in animals on diet B.

Lateral ventricle infusions of abeta induce a reduction in activity. These effects were completely diminished by feeding the present treatment diet. The beneficial effects are indicative for the advantageous used of the present composition in the present method, particularly for improving instrumental and/or basic activities of daily living.

Example 2

Compositions with Package

Packaged composition comprising per 125 ml:
Energy 125 kcal; Protein 3.9 g; Carbohydrate 16.5 g; Fat 4.9 g.
Fat includes 1.5 g DHA+EPA, and 106 mg phospholipids (soy lecithin); Choline 400 mg; UMP (uridine monophosphate) 625 mg; Vitamin E 40 mg α-TE; Vitamin C 80 mg; Selenium 60 µg; Vitamin B12 3 µg; Vitamin B6 1 mg; Folic acid 400 µg.
Minerals and trace elements: Sodium 125 mg; Potassium 187.5 mg; Chloride 156.3 mg; Calcium 100 mg; Phosphorus 87.5 mg; Magnesium 25 mg; Iron 2 mg; Zinc 1.5 mg; Copper 225 µg; Manganese 0.41 mg; Molybdenum 12.5 µg; Chromium 8.4 µg; Iodine 16.3 µg.
Vitamins: Vit. A 200 µg-RE; vit. D3 0.9 µg; vit. K 6.6 µg; Thiamin (B1) 0.19 mg; Riboflavin (B2) 0.2 mg; Niacin (B3) 2.25 mg-NE; Pantothenic acid (B5) 0.66 mg; Biotin 5 µg.

The package indicates that the composition improves the activities of daily living, particularly stimulating independent walking, bathing, grooming, dressing, use of communication equipment (particularly telephone), use of household appliances (particularly television), cleaning dishes, preparation of meal or drink and/or writing. The composition is suitable for administration to patients suffering from dementia or Alzheimer's disease.

Example 3

In vivo Study

Rats were fed diets specific in B-vitamins (vitamin $B_6$, vitamin $B_{12}$, and folic acid) content during four weeks. One group was fed a diet deficient of B vitamins and the other group was fed a B-vitamin enriched diet. The rats were housed in groups of four and locomotor activity was assessed in the home cages. The average percentage of the change in activity between the four week intervention period and a control period was calculated.

During the sleep (inactive) period, the average change in activity was decreased in rats fed the B-vitamin enriched diet as compared to the B-vitamin deficient diet (p=0.046). In fact, the locomotor activity increased in the rats fed the B-vitamin deficient diet, while it decreased in the rats fed the B-vitamin enriched diet as compared to the control period. Locomotor activity was increased during the sleep period of the rat by feeding a B-vitamin deficient diet. In contrast, activity during the sleep period was decreased by feeding B-vitamin enriched diet. This indicates that rats show a disturbed sleeping pattern when a B-vitamin deficiency is induced. Hence, wellbeing is affected by the B-vitamin deficient diet, as a disturbed sleeping pattern most likely decreases wellbeing. In contrast, wellbeing was improved in rats fed the B-vitamin enriched diet: locomotor activity was decreased and therefore time spent at rest increased.

Example 5

Clinical Study

The present study was performed to assess the effect of an intervention with a medical food on activities of daily living in Alzheimer's Disease (AD) subjects. 212 subjects were randomly allocated in a double-blind 12 weeks study to receive a 125 ml (125 kcal) once-a-day milk-based drink with: (a) the formula according to Example 2 (active product) or (b) an iso-caloric control drink (control product) according to Example 2, but without EPA, DHA, phospholipids, choline, UMP, vitamin E, vitamin C, selenium, vitamin B12, vitamin B6 and folic acid. Outcome measure was an ADCS-ADL Inventory (Alzheimer's Disease Cooperative Study—Activities of Daily Living).

Activities of daily living were measured using the Alzheimer's Disease Cooperative Study Activities of Daily Living Inventory (ADCS-ADL). This is a caregiver rated questionnaire of 23 items, with possible scores over a range of 0-78, where 78 implies full functioning with no impairment. The ADCS-ADL assesses functional capacity across a wide spectrum of severity and was the primary tool for collecting ADL data for this study population.

Figure 2:
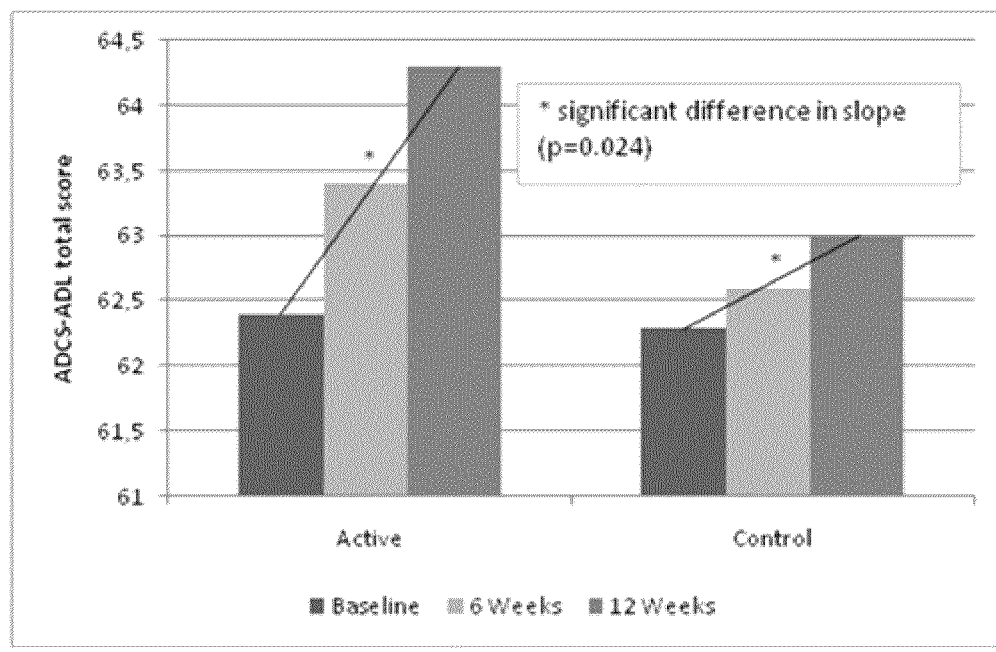
FIG. 2 shows the ADCS-ADL score over a 12 weeks intervention period of Alzheimer's patients treated with a product according to Example 2 vs a control.

Results:

At baseline, there was no significant difference between the group treated with the active product and the group treated with the control product. However, there was a significant difference between the two groups in the increase in ADCS-ADL score over the 12 weeks intervention period (p=0.024). The control group (n=106) had an average improvement of +0.72 points, whereas the active group (n=106) had an average improvement of +1.85 points on the ADCS-ADL scale (FIG. 2).

The improved ADCS-ADL score over 12 weeks was mainly the result of an improvement in instrumental activities.

This study demonstrates that intervention with the active product of Example 2 for 12 weeks improves activities of daily living.

What is claimed:

1. A method for supporting activities of daily living of a subject suffering from Alzheimer's disease or dementia and/or dementing elderly comprising administering to said subject or elderly a liquid composition having an osmolality of 300 to 800 mOsm/kg and comprising:
   (a) DHA and/or EPA, and
   (b) uridine, or its equivalent.

2. A method for supporting activities of daily living of non-dementing elderly comprising administering to said elderly a composition comprising:
   (a) DHA and/or EPA, and
   (b) uridine, or its equivalent.

3. The method according to claim 1, wherein the activities of daily living are measured using the Alzheimer's Disease Cooperative Study Activities of Daily Living Inventory (ADCS-ADL).

4. The method according to claim 1, wherein the subject is a human suffering from Alzheimer's disease and having a mini mental state examination (MMSE) score between 16 and 27.

5. The method according to claim 1, wherein the composition further comprises folic acid, vitamin B12, vitamin B6, or a combination thereof.

6. The method according to claim 1, wherein the activities comprise the ability for:
- eating, walking, toileting, bathing, grooming or dressing; or
- use of communication equipment, making conversations, keeping appointments, use of household appliances, cleaning dishes, preparation of meal or drink, writing, reading, independent housekeeping, transportation or shopping.

7. The method according to claim 1, wherein the composition comprises 0.1-2 g uridine, calculated as uridine monophosphate, per daily dosage unit.

8. The method according to claim 1, wherein the composition comprises 300-3600 mg DHA per daily dosage unit.

9. The method according to claim 1, wherein the composition further comprises arachidonic acid (AA).

10. The method according to claim 9, wherein the composition has a DHA to AA weight ratio of at least 2.0.

11. The method according to claim 1, wherein the composition is a liquid with a viscosity of 1-40 mPa·s measured at a shear rate of 100 per sec at 20° C.

12. The method according to claim 1, wherein the composition further comprises 80-2000 mg choline per daily dosage unit.

13. A liquid composition comprising per 100 ml:
(a) 0.2-2 gram uridine or an uridine equivalent;
(b) 0.5-5 g DHA;
(c) 0.5-10 g protein;
(d) 2-20 g carbohydrates;
(e) 0.5-15 µg vitamin B12;
(f) 50-1000 µg folic acid;
(g) 0.1-10 mg vitamin B6; and
(h) 50 mg-3 g choline,
wherein the composition has a viscosity of 1-40 mPas measured at a shear rate of 100 per sec at 20° C.; an osmolality of 300 to 800 mOsm/kg; and a caloric density between 0.2 and 3 kcal/ml.

\* \* \* \* \*